(12) United States Patent
Yoshida et al.

(10) Patent No.: US 10,813,610 B2
(45) Date of Patent: Oct. 27, 2020

(54) PROXIMITY OPERATION X-RAY FLUOROSCOPIC IMAGING APPARATUS

(71) Applicant: SHIMADZU CORPORATION, Kyoto (JP)

(72) Inventors: Koji Yoshida, Kyoto (JP); Takayoshi Okamura, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 16/224,917

(22) Filed: Dec. 19, 2018

(65) Prior Publication Data

US 2019/0374180 A1    Dec. 12, 2019

(30) Foreign Application Priority Data

Jun. 11, 2018    (JP) ................................. 2018-110858

(51) Int. Cl.
*A61B 6/00* (2006.01)
*H04N 5/32* (2006.01)

(52) U.S. Cl.
CPC ............ *A61B 6/4452* (2013.01); *A61B 6/487* (2013.01); *A61B 6/588* (2013.01); *A61B 6/4464* (2013.01); *H04N 5/32* (2013.01)

(58) Field of Classification Search
CPC ....... A61B 6/4452; A61B 6/487; A61B 6/588; A61B 6/4464; H04N 5/32
See application file for complete search history.

(56) References Cited

U.S. PATENT DOCUMENTS

2008/0247516 A1* 10/2008 Fink ..................... A61B 6/4464
378/194

FOREIGN PATENT DOCUMENTS

| JP | 10-43169 | 2/1998 |
| JP | 2001-057971 | 3/2001 |
| JP | 2001057971 A * | 3/2001 |

* cited by examiner

*Primary Examiner* — Courtney D Thomas
(74) *Attorney, Agent, or Firm* — Andrew F. Young, Esq.; Lackenbach Siegel, LLP

(57) ABSTRACT

A proximity operation fluoroscopic imaging apparatus allows a retreating operation for a X-ray detection element at an arbitrarily-positioned height. The X-ray imaging is carried out using the proximity operation fluoroscopic imaging apparatus a hanging-type X-ray irradiation element, a deck unit 26, supporting a flat panel detector 13, moves to a retreating position. The deck unit 26, supports a flat panel detector 13, and enables a retreating operation in the area of a subject M side of a tower unit 25, so that such a retreating operation is feasible regardless a height-position of the deck unit 26 supports the flat panel detector 13.

2 Claims, 9 Drawing Sheets

PROXIMITY OPERATION X-RAY FLUOROSCOPIC IMAGING APPARATUS

CROSS REFERENCE TO RELATED APPLICATIONS

This application relates to, and claims priority from JP 2018-110858 filed Jun. 11, 2018 the entire contents of which are incorporated herein by reference.

FIGURE SELECTED FOR PUBLICATION

FIG. 4

BACKGROUND OF THE INVENTION

Field of the Invention

The present invention relates to a radiation fluoroscopy imaging apparatus that performs an X-ray fluoroscopy and an X-ray imaging, and particularly, relates to a proximity operation fluoroscopic imaging apparatus.

Description of the Related Art

According to such a proximity operation fluoroscopic imaging apparatus, the operator carries out the X-ray fluoroscopy in the proximity position of the apparatus and the operator operates a handle of the operation unit when moving the imaging system comprising such as an X-ray tube, a collimator and an X-ray detection element. In addition, such a proximity operation fluoroscopic imaging apparatus is applied to carry out the X-ray imaging using the X-ray irradiation unit hanging from the ceiling, so that a second X-ray detection element such as a cassette and a flat panel detector housing an X-ray film inside thereof is attachable thereto.

FIG. 6 is a front view of a conventional proximity operation fluoroscopic imaging apparatus, illustrating the state in which an X-ray fluoroscopy is carried out and FIG. 7 is a side view thereof.

Such a proximity operation fluoroscopic imaging apparatus comprises: a main unit 22 having a table 23 on which a subject M is loaded; a base 21 that supports the main unit 22; an X-ray tube 11 that is placed at the reverse side of the subject M which is loaded on the table 23, i.e., under the table 23; an X-ray irradiation unit comprising a collimator 12 connected with the X-ray tube 11; a tower unit 25 placed at the side of the table 23; a floater 27 that moves along the tower unit 25; a deck unit 26, which is an arm, that moves in the direction crossing the moving direction of the floater 27 while being guided by the floater 27. The tower unit 25 and the X-ray tube 11 have connected to each other with a connection element 24 and the tower unit 25 and the X-ray tube 11 and the collimator 12 move reciprocally in the body-axis direction (right-and-left direction in FIG. 6 and vertical direction to the paper in FIG. 7) of the subject M in synchronism with each other.

The floater 27 has an approximate L-shape in the side view thereof. The tower unit 25 comprises a guide member such as a rail, not shown in FIG., so that the floater 27 is movable along the tower unit 25 in accordance with the action of the guide member. In addition, the deck unit 26 also comprises a guide member such as a rail, not shown in FIG., so that the deck unit 26 is movable along the floater 27 in accordance with the action of the guide member.

The deck unit 26 supports an X-ray detector consisting of an image intensifier (II) 18 and a camera 19. In addition, an operation unit 29 that is used when the deck unit 26 moves with the X-ray detection unit comprising the image intensifier 18 and the camera 19 is attached to the tip of the deck unit 26. In addition, the main unit 22 comprises a second X-ray detection element 14 that is used when a hanging-type X-ray irradiation element, described later, is used for the X-ray imaging. The second detection element 14 comprises such as a cassette housing the X-ray film and a flat panel detector.

On the other hand, the hanging-type X-ray irradiation element used with the proximity operation fluoroscopic imaging apparatus comprises the X-ray tube 15 and the collimator 16 connected with the X-ray tube 15.

The X-ray tube 15 is supported by the supporting element 32 having a telescopic (nested) structure and the supporting element 32 is supported by the moving element 31 that is movable in the two directions orthogonal to each other in accordance with the rail mechanism, not shown in FIG., attached to the ceiling 30. Such a hanging-type X-ray irradiation element is also used for an X-ray imaging using the wall stand or the lying table, not shown in FIG.

FIG. 8 is a front view illustrating the state in which an X-ray imaging is carried out using the conventional proximity operation fluoroscopic imaging apparatus and the hanging-type X-ray irradiation element, and FIG. 9 is a side view thereof. In addition, according to FIGs., the state in which the imaging of a proximity of the abdomen of the subject M is being carried out using the hanging-type X-ray irradiation element.

The image intensifier 18 and the camera 19 that are not used when the hanging-type X-ray irradiation element is applied to the X-ray imaging must be retreated to the position where the X-ray imaging using the hanging-type X-ray irradiation element is not obstructed thereby. Therefore, referring to FIG. 8, first, the deck unit 26 supporting the image intensifier 18 and the camera 19 moves toward the head of the subject M along with the tower unit 25 and the floater 27. Then, referring to FIG. 9, the image intensifier 18 and the camera 19 move to the tower unit 25 side along with the deck unit 26.

Accordingly, referring to FIG. 8, FIG. 9, the X-ray tube 15 and the collimator 16 relative to the hanging-type X-ray irradiation element are in-place right above the subject M. In addition, the second X-ray detection element 14 is in-place at the position facing the X-ray tube 15 and the collimator 16 relative to the hanging-type X-ray irradiation element.

RELATED PRIOR ART DOCUMENTS

Patent Document

Patent Document 1: JP Patent Published 2001-57971 A1

ASPECTS AND SUMMARY OF THE INVENTION

Objects to be Solved

Generally, the image intensifier 18 and the camera 19 are quite heavy. Therefore, the deck unit 26 and the floater 27 that support the image intensifier 18 and the camera 19 must be in an appropriated size and have strength, and the slidable area of the deck unit 26 and the floater 27 must be secured so as to provide enough space for the size thereof. To accommodate such a requirement, referring to FIG. 9, when the image intensifier 18 and the camera 19 move to the tower unit 25 side along with the deck unit 26, the tip of the deck unit 26, which is in the opposite side of the subject M, projects to the opposite side of the subject M farther than the tower unit 25.

Referring to FIG. 9, the deck unit 26 and the floater 27 have such a structure, so that when the image intensifier 18 and the camera 19 move to the tower unit 25 side along with the deck unit 26, the deck unit 26 must first move over the top-end of the tower unit 25 followed by moving the deck unit 26 to the side of the tower unit 25. Specifically, when retreating the image intensifier 18 and the camera 19, the deck unit 26 must be in-place over the top-end of the tower unit 25, i.e., at least at the top-end position of the up-and-down stroke.

The operator has to grip the operation unit 29 to facilitate moving when the image intensifier 18 and the camera 19 are moved along with the deck unit 26, so that it is extremely hard to operate the operation unit 29 while placing the deck unit 26 over the top-end of the tower unit 25, and particularly, in case of such that the operator is short, such as a step may be needed. To avoid such a situation, the height of the tower unit 25 must be limited in case.

The present invention has been completed to solve the above problem and the purpose of the present invention is to provide a proximity operation fluoroscopic imaging apparatus that is feasible that the retreating operation for the X-ray detection element is carried out in an arbitrarily-positioned height.

Means for Solving the Problem

According to the claimed invention, a proximity operation fluoroscopic imaging apparatus comprises: a main unit comprising a table on which a subject is loaded; an X-ray irradiation element that is in-place in the opposite side of the subject so as to sandwich the table; a tower unit that is in-place in a side of the table; a floater that moves along the tower unit; a deck unit that moves in an orthogonal direction crossing a moving direction of the floater while guided by the floater; a first X-ray detection element that the deck unit supports; a second X-ray detection element that is in-place in the main unit is used when a hanging-type X-ray irradiation element is used for the X-ray imaging; wherein the first X-ray detection element is a flat panel detector, and the floater guides the deck unit supporting the flat panel detector in the rather subject side area than the surface of the subject side of the tower unit so that the floater guides the deck unit so as to move in the direction crossing the moving direction of the floater.

According to another aspect of the present invention claimed in claim, the X-ray irradiation element further comprises a rotation mechanism that rotates the main unit, the flat panel detector around the central axis facing a horizontal direction.

Effects of the Present Invention

According to the aspect of the present invention claimed in claim, the first flat panel detector is lightweight, so that the sliding area of the deck unit and the floater that support the flat panel detector can be smaller and the deck unit becomes movable in the direction crossing the moving direction of the floater in the area of the rather subject side than the surface of the subject side of the tower unit. Accordingly, the retreating operation can be carried out at the arbitrarily-positioned height, so that the operability of the apparatus by the operator can be unexceptionally improved. In addition, in accordance with such an improvement, the height of the tower unit 25 can be set higher and as a result, the distance space between the table and the flat panel detector can be fully secured, so that flexibility and freedom of the X-ray fluoroscopy and the X-ray imaging can be boosted.

According to the another aspect of the present invention claimed in claim, when moving the X-ray irradiation element, the main unit and in addition, the flat panel detector are rotated around the central-axis facing the horizontal direction and preforming the X-ray fluoroscopy or X-ray imaging while placing the table surface in the vertical direction, the distance space between the table and the flat panel detector can be fully secured, so that even when the X-ray fluoroscopy or the X-ray imaging for the subject sitting on the wheel chair, the present invention facilitates to carry out the X-ray fluoroscopy and the X-ray imaging.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Figure 1:
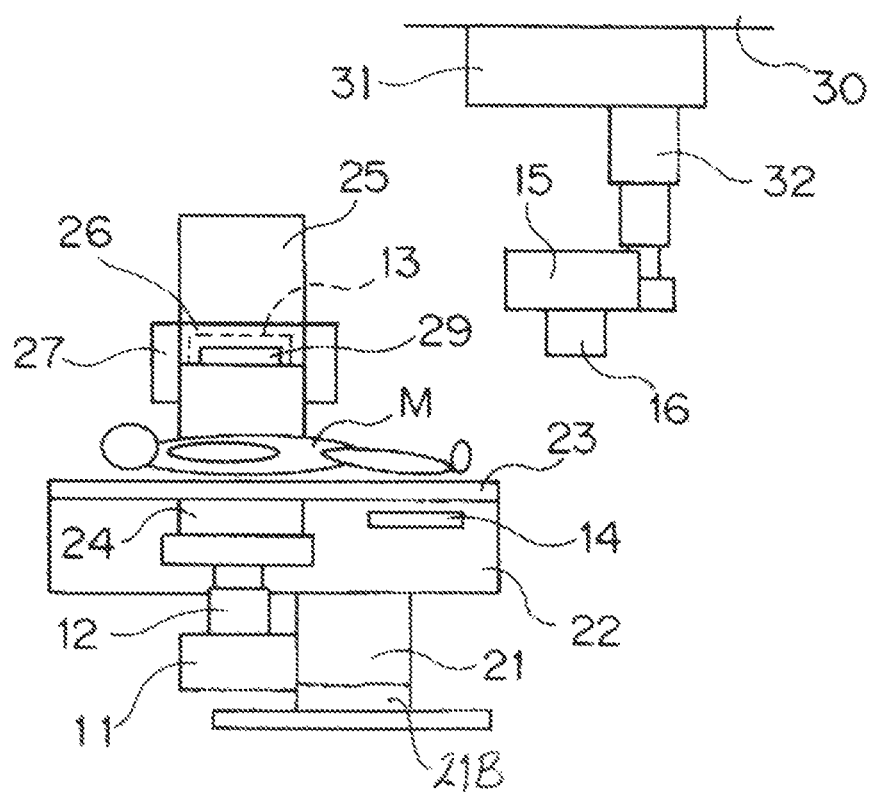
FIG. 1 is a front view illustrating the state in which an X-ray fluoroscopy is carried out using a proximity operation fluoroscopic imaging apparatus of the present invention.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

Figure 2:
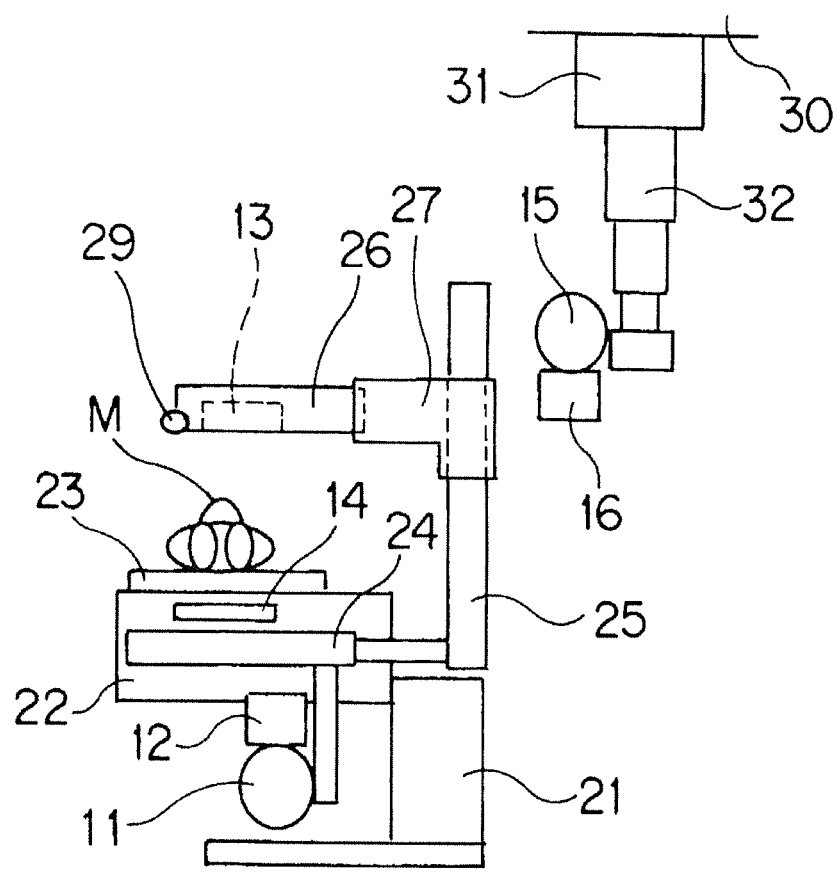
FIG. 2 is a side view illustrating the state in which an X-ray fluoroscopy is carried out using a proximity operation fluoroscopic imaging apparatus of the present invention.

The inventors set forth Embodiments of the present invention based on the following FIGs. FIG. 1 is the front view illustrating the state in which an X-ray fluoroscopy is carried out using the proximity operation fluoroscopic imaging apparatus of the present invention, and FIG. 2 is a side view thereof.

As well as the conventional proximity operation fluoroscopic imaging apparatus, such a proximity operation fluoroscopic imaging apparatus, comprises: a main unit 22 having a table 23 on which a subject M is loaded; a base 21 that supports the main unit 22; an X-ray tube 11 that is placed at the reverse side of the subject M who is loaded on the table 23, i.e., under the table 23; an X-ray irradiation unit comprising a collimator 12 connected with the X-ray tube 11; a tower unit 25 placed at the side of the table 23; a floater 27 that moves along the tower unit 25; a deck unit 26, which is an arm, that moves in the direction crossing a moving direction of the floater 27 while being guided by the floater 27. The tower unit 25 and the X-ray tube 11 have connected to each other with a connection element 24 and the tower unit 25 and the X-ray tube 11 and the collimator 12 move reciprocally in the body-axis direction (right-and-left direction in FIG. 1 and vertical direction to the paper in FIG. 2) of the subject M in synchronism with each other.

The floater 27 has an approximate L-shape in the side view thereof. The tower unit 25 comprises a stopping guide member 27A such as a rail, so that the floater 27 is movable along the tower unit 25 in accordance with the action of the stopping guide member 27A. In addition, the deck unit 26 also comprises a guide member such as a rail, not shown in FIG., so that the deck unit 26 is movable along the floater 27 in accordance with the action of the stopping guide member 27A.

The deck unit 26 supports the flat panel detector 13 as the first X-ray detection element. In addition, the operation unit 29 that is used when the deck unit 26 moves with the flat panel detector 13 is attached to the tip of the deck unit 26. In addition, the main unit 22 comprises the second X-ray detection element 14 that is used when the hanging-type X-ray irradiation element is used for the X-ray imaging. The second detection element 14 comprises such as a cassette housing the X-ray film and a flat panel detector.

In addition, the X-ray irradiation element comprising the X-ray tube 11 and the collimator 12, the main unit 22, and the flat panel detector 13 are rotatable around the central-axis facing the horizontal direction using the rotation mechanism 21B, installed in the base 21. At this time, the surface of the table 23 will face the vertical direction, so that e.g., the X-ray fluoroscopy becomes feasible for the erect subject M.

The hanging-type X-ray irradiation element used with the proximity operation fluoroscopic imaging apparatus comprises the X-ray tube 15 and the collimator 16 connected with the X-ray tube 15. The X-ray tube 15 is supported by the supporting element 32 having the telescopic structure and the supporting element 32 is supported by the moving element 31 that is movable in the two directions orthogonal to each other in accordance with the rail mechanism, not shown in FIG., attached to the ceiling 30. Such a hanging-type X-ray irradiation element is also used for an X-ray imaging using the wall stand or the lying table, not shown in FIG.

Figure 3:
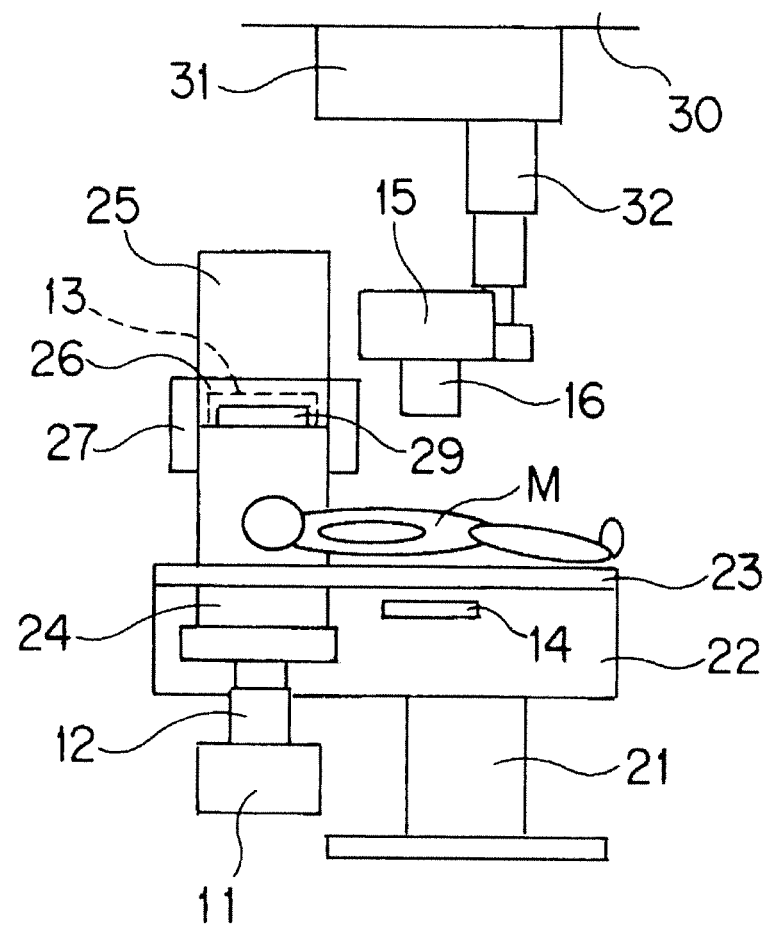
FIG. 3 is a front view illustrating the state in which an X-ray imaging is carried out using the proximity operation fluoroscopic imaging apparatus of the present invention and the hanging-type X-ray irradiation element thereof.
Figure 4:
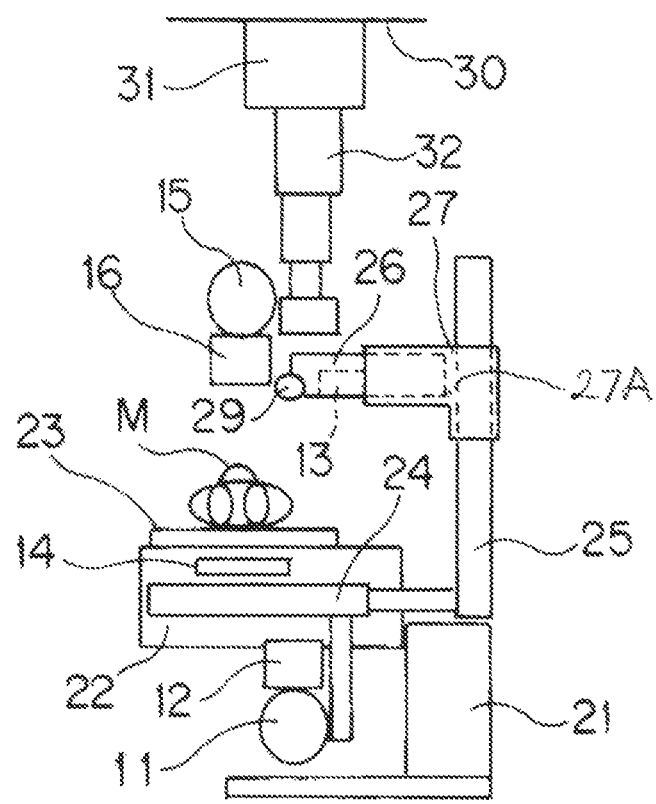
FIG. 4 is a side view illustrating the state in which an X-ray imaging is carried out using the proximity operation fluoroscopic imaging apparatus of the present invention and the hanging-type X-ray irradiation element thereof.

FIG. 3 is the front view illustrating the state in which an X-ray imaging is carried out using the proximity operation fluoroscopic imaging apparatus of the present invention and the hanging-type X-ray irradiation element thereof, and FIG. 4 is the side view thereof. In addition, according to FIGs., the state, in which the imaging of a proximity of the abdomen of the subject M is being carried out using the hanging-type X-ray irradiation element, is illustrated.

The weight of the flat panel detector 13 is extremely light compared to the image intensifier 18 and the camera 19. Therefore, the deck unit 26 and the floater 27 that support the flat panel detector 13 can be designed as a smaller size and a lesser strength than the conventional structure in which the image intensifier 18 and the camera 19 are used without any particular problem, so that the sliding area of the deck unit 26 and the floater 27 can be made smaller. Accordingly, referring to FIG. 2, FIG. 4, the floater 27 enables guiding the deck unit 26, supporting the flat panel detector 13, so as to move in the direction crossing the up-and-down direction of the floater 27 in the area from the surface, facing the subject M, of the tower unit 25 toward the subject M.

Referring to FIG. 2, FIG. 4, when the deck unit 26 and the floater 27 enable guiding the deck unit 26 so as to move in the direction crossing the up-and-down direction of the floater 27 in the area from the surface, facing the subject M, of the tower 25 toward the subject M, the deck unit 26 that support the flat panel detector 13 can be moved to the waiting position at which the X-ray imaging for the subject M is carried out using the hanging-type X-ray irradiation element in the state in which the deck unit 26 and the floater 27 are in-place in the arbitrarily-positioned height.

Referring to FIG. 3, when the X-ray imaging is carried out using the proximity operation fluoroscopic imaging apparatus of the present invention and the hanging-type X-ray irradiation element thereof, the deck unit 26, supporting the flat panel detector 13, moves toward the head of subject M along with the tower unit 25 and the floater 27. Then, referring to FIG. 4, the flat panel detector 13 moves toward the tower unit 25 side along with the deck unit 26. Accordingly, referring to FIG. 3, FIG. 4, the X-ray tube 15 and the collimator 16 relative to the hanging-type X-ray irradiation element are in-place right above the subject M. In addition, the second X-ray detection element 14 is in-place at the position facing the X-ray tube 15 and the collimator 16 relative to the hanging-type X-ray irradiation element.

At this time, referring to FIG. 2, FIG. 4, the deck unit 26, supporting the flat panel detector 13, enables retreating within the area from the surface, facing the subject M, of the tower 25 toward the subject M, so that such a retreating operation can be carried out regardless the height-position of the deck unit 26 supporting the flat panel detector 13. Therefore, the deck unit 26 is not required to move higher than the top-end of the tower unit 25 so as to carry out the retreating operation, so that the operation required for the conventional proximity operation fluoroscopic imaging apparatus using the image intensifier 18 and the camera 19 is not required. Accordingly, the operator can carry out easily such a retreating operation.

In addition, the deck unit 26 is not required to move higher than the top-end of the tower unit 25 so as to carry out the retreating operation, so that the operation required for the conventional proximity operation fluoroscopic imaging apparatus using the image intensifier 18 and the camera 19 is not required, and as a result, the deck unit 26 can be designed to have a sufficient height therefor without a particular concern. Therefore, the deck unit 26 can be arbitrarily structured in accordance with the SID (Source Image Receptor Distance).

Figure 5:
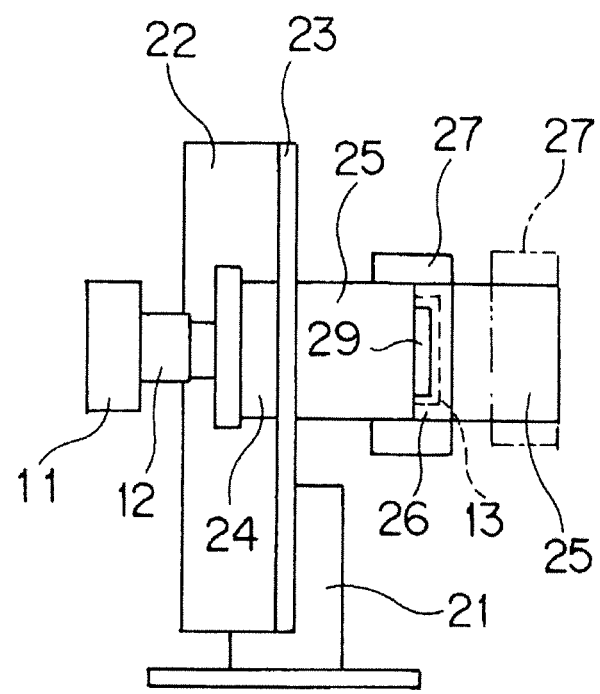
FIG. 5 is a schematic view illustrating the X-ray fluoroscopy while the surface of the table 23 facing the vertical direction using the proximity operation fluoroscopic imaging apparatus of the present invention.
Figure 6:
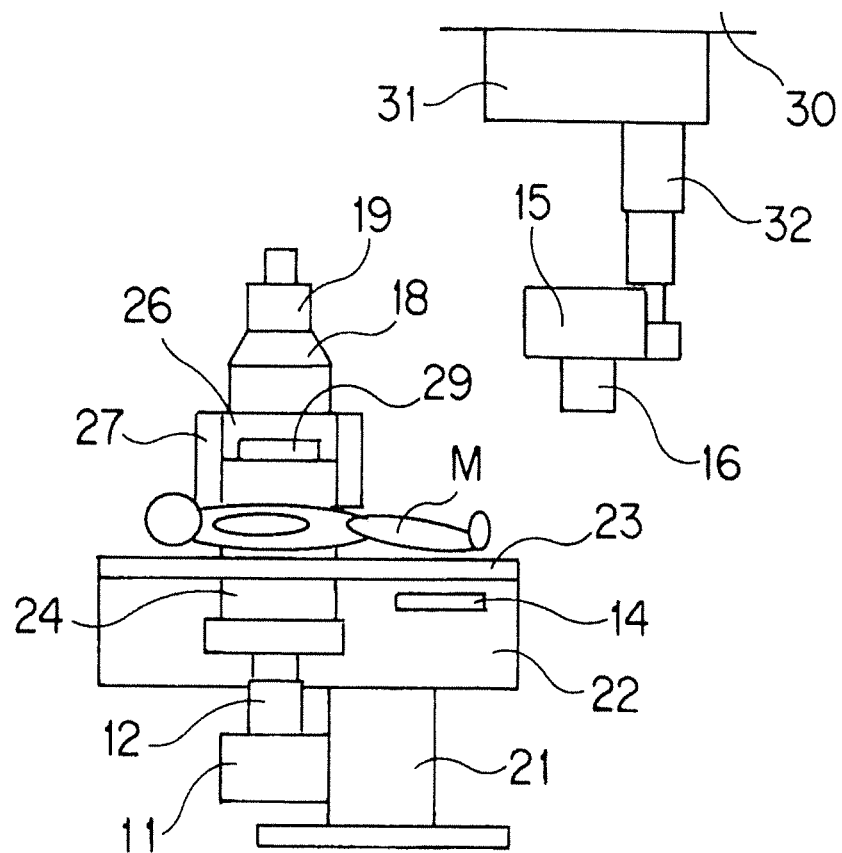
FIG. 6 is a front view illustrating the state in which an X-ray fluoroscopy is carried out using a conventional proximity operation fluoroscopic imaging apparatus.
Figure 7:
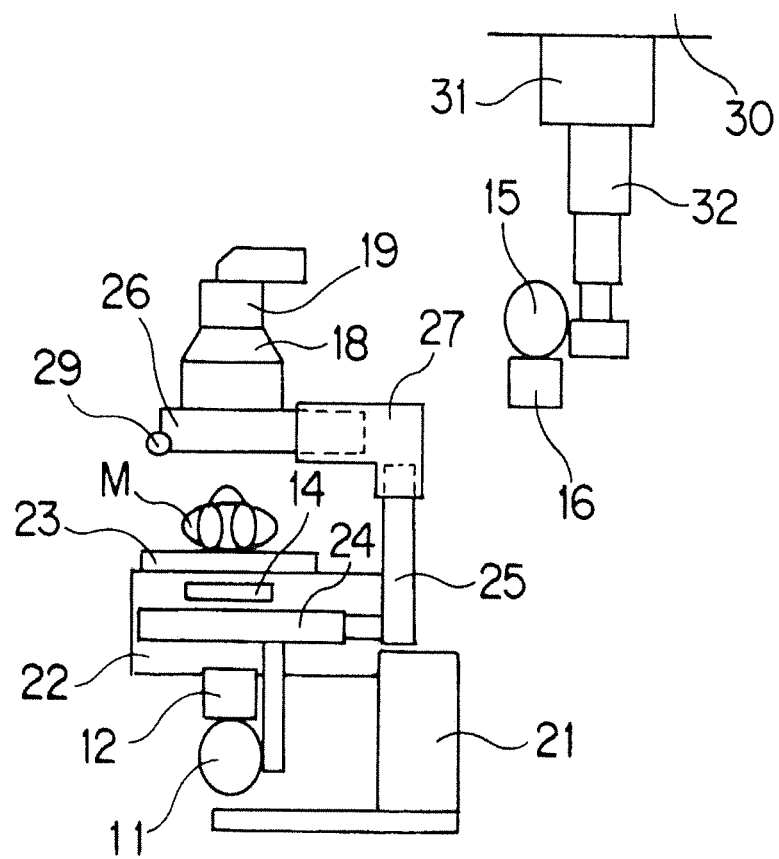
FIG. 7 is a side view illustrating the state in which an X-ray fluoroscopy is carried out using a conventional proximity operation fluoroscopic imaging apparatus.
Figure 8:
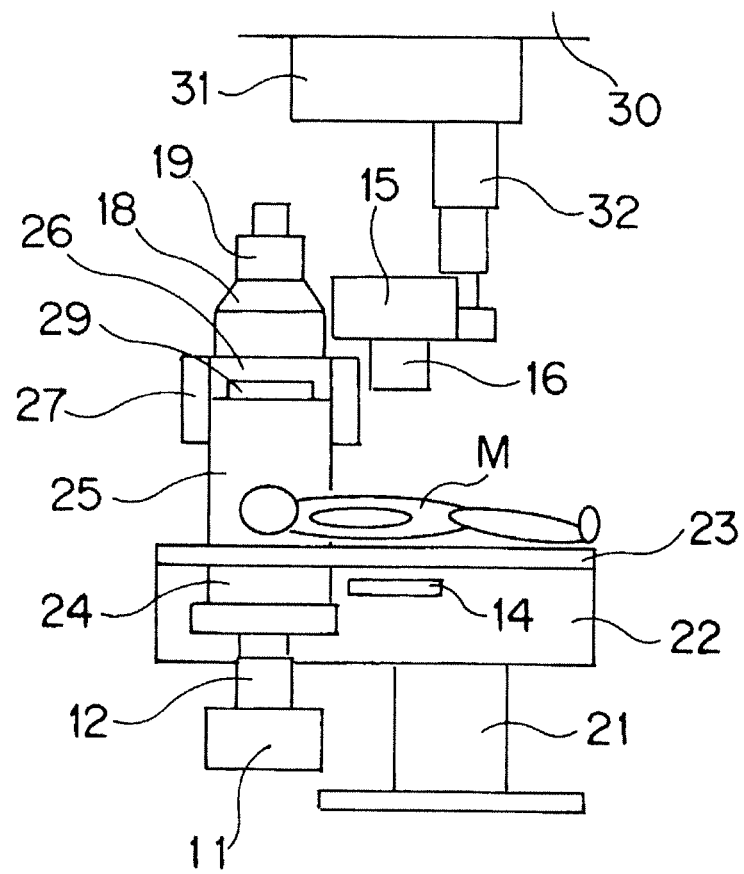
FIG. 8 is a front view illustrating the state in which an X-ray imaging is carried out using the conventional proximity operation fluoroscopic imaging apparatus of the present invention and the hanging-type X-ray irradiation element thereof.
Figure 9:
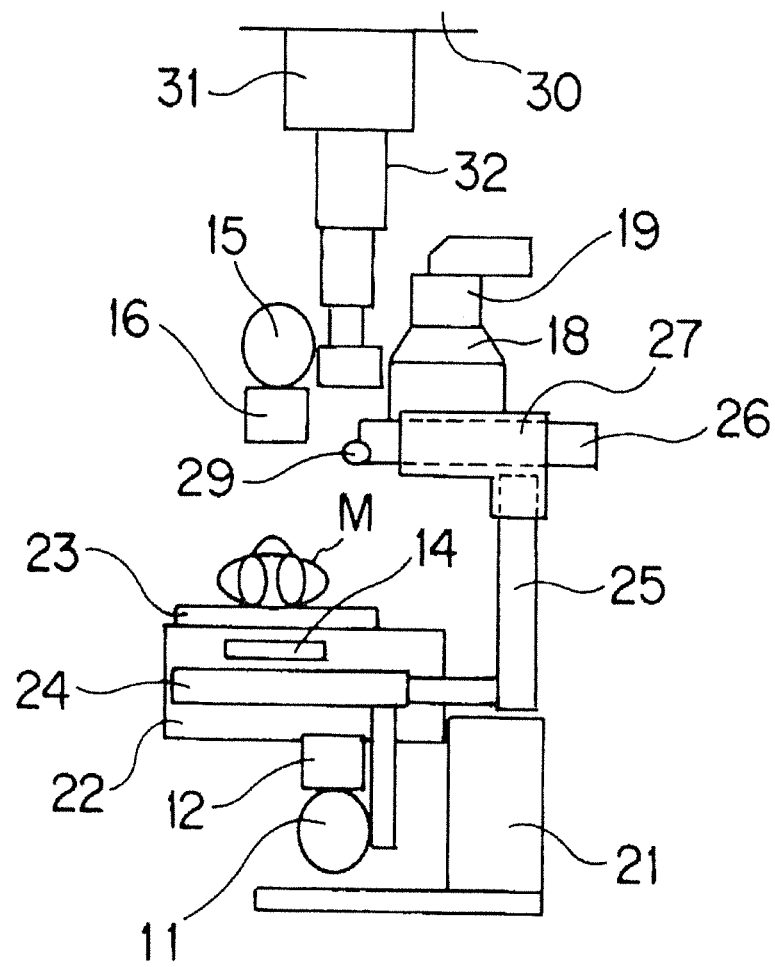
FIG. 9 is a side view illustrating the state in which an X-ray imaging is carried out using the conventional proximity operation fluoroscopic imaging apparatus of the present invention and the hanging-type X-ray irradiation element thereof.

FIG. 5 is the schematic view illustrating the X-ray fluoroscopy while the surface of the table 23 facing the vertical direction using the proximity operation fluoroscopic imaging apparatus of the present invention.

For example, when an imaging swallowing exam for the sitting subject M on the wheel chair is carried out, the X-ray fluoroscopy can be carried out as-is in such a posture. At this time, referring to FIG. 5, the floater 27 is in-place at the far-right position, indicated by the broken virtual line, and the SID is set up larger, so that even when a large wheel chair is used, the X-ray fluoroscopy becomes feasible as-is.

In addition, when the SID is set up larger, the erect chest imaging become feasible.

In addition, when the SID is further adjusted by combining the tube back-and-forth operation of the X-ray tube 15 and the collimator 16 in the right-and-left direction referring to FIG. 5, the exchange of the grid may be unnecessary.

REFERENCE OF SIGNS

11 X-ray tube
12 Collimator
13 Flat panel detector
14 Second X-ray detector
15 X-ray tube
16 Collimator
21 Base
22 Main unit
23 Table
25 Tower unit
26 Deck unit
27 Floater
M Subject As used herein, a computerized or computer-type system comprises an input device for receiving data in any form, an output device for outputting data in any form (e.g. X-ray image or other-ray-image-data, data transmission, printing or displaying on a display screen, etc, without limitation), a memory for storing data as well as computer code, and a processor/microprocessor (the same) for executing computer code wherein said computer code resident in said memory to cause the processor/microprocessor to read-in data, process said data within said microprocessor and output said processed data via said output device.

It will be understood that the discussed any elements, circuits, detectors, switches, etc. will be understood to be functional as arranged herein in their functional locations without the need for minute disclosure of particular sub-components, resistors, capacitors, links, pc-boards, etc., as would be understood by one of skill in this particular art.

It will be further understood by those of skill in the art that the apparatus and devices and the elements herein, without limitation, and including the sub components such as operational structures, circuits, communication pathways, and related elements, control elements of all kinds, circuits, elements, features, display circuits and display systems and elements, any necessary driving elements, inputs, sensors, detectors, memory elements, processors and any combinations of these structures etc. as will be understood by those of skill in the art as also being identified as or capable of operating the systems and devices and subcomponents noted herein and structures that accomplish the functions without restrictive language or label requirements since those of skill in the art are well versed in related radiation imaging devices, computer and operational controls and technologies of radiographic devices and all their sub components, including various circuits and combinations of circuits without departing from the scope and spirit of the present invention.

Although only a few embodiments have been disclosed in detail above, other embodiments are possible and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

Those of skill would further appreciate that the various illustrative logical blocks, modules, circuits, and algorithm steps described in connection with the embodiments disclosed herein may be implemented as electronic hardware, computer software running on a specific purpose machine that is programmed to carry out the operations described in this application, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the exemplary embodiments.

The various illustrative logical blocks, modules, and circuits described in connection with the embodiments disclosed herein, may be implemented or performed with a general or specific purpose processor, or with hardware that carries out these functions, e.g., a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. The processor/microprocessor etc. can be part of a computer system that also has an internal bus connecting to cards or other hardware, running based on a system BIOS or equivalent that contains startup and boot software, system memory which provides temporary storage for an operating system, drivers for the hardware and for application programs, disk interface which provides an interface between internal storage device(s) and the other hardware, an external peripheral controller which interfaces to external devices such as a backup storage device, and a network that connects to a hard wired network cable such as Ethernet or may be a wireless connection such as a RF link running under a wireless protocol such as 802.11. Likewise, an external bus may be any of but not limited to hard wired external busses such as IEEE-1394 or USB. The computer system can also have a user interface port that communicates with a user interface, and which receives commands entered by a user, and a video output that produces its output via any kind of video output format, e.g., VGA, DVI, HDMI, display port, or any other form. This may include laptop or desktop computers, and may also include portable computers, including cell phones, tablets such as the IPAD™ and Android™ platform tablet, and all other kinds of computers and computing platforms.

A processor may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein.

The steps of any method or algorithm described in connection with the embodiments disclosed herein may be embodied directly in hardware, in a software module executed by a processor, using cloud computing, or in combinations, and in any type of non-transitory memory. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of tangible storage medium that stores tangible, non-transitory computer based instructions. An exemplary storage medium is coupled to the processor such that the processor can read information from, and write information to, the storage medium. In the alternative, the storage medium may be integral to the processor. The processor and the non-transitory storage medium may reside in reconfigurable logic of any type.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer.

The memory storage can also be rotating magnetic hard disk drives, optical disk drives, or flash memory based storage drives or other such solid state, magnetic, or optical storage devices. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media. The computer readable media can be an article comprising a machine-readable non-transitory tangible medium embodying information indicative of instructions that when performed by one or more machines result in computer implemented operations comprising the actions described throughout this specification.

Operations as described herein can be carried out on or over a web site. The website can be operated on a server computer, or operated locally, e.g., by being downloaded to the client computer, or operated via a server farm. The website can be accessed over a mobile phone or a PDA, or on any other client. The website can use HTML code in any form, e.g., MHTML, or XML, and via any form such as cascading style sheets ("CSS") or other.

The computers described herein may be any kind of computer, either general purpose, or some specific purpose computer such as a workstation. The programs may be written in C, or Java, Brew or any other programming language. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

Also, the inventors intend that only those claims which use the words "means for" are intended to be interpreted under 35 USC 112(f), only when the word 'for' is combined with 'means' in the claim. Moreover, no limitations from the specification are intended to be read into any claims, unless those limitations are expressly included in the claims.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. A proximity operation fluoroscopic imaging apparatus, comprising:
   a table on which a subject is loaded;
   said table having a first side and a second side, said subject being on said first side of said table;
   a first X-ray irradiation element that is in-place at said second side of said table and opposite said subject so as to sandwich said table;
   a tower unit that is in-place along a side of said table;
   a floater that moves along said tower unit;
   a deck unit that moves in an orthogonal direction crossing a moving direction of said floater while being guided by said floater;
   a main unit;
   a first X-ray detection element that is in-place in said main unit that is used when a hanging-type X-ray irradiation element is used for an X-ray imaging;
   said first X-ray detection element is a flat panel detector and said floater guides said deck unit supporting said flat panel detector in an area from a surface, facing said subject, of said tower unit toward said subject so that said floater guides said deck unit so as to move said deck unit in a direction crossing a moving direction of said floater; and said floater further includes a stopping guide member configured to engage said tower unit and suspend a motion of said deck unit before reaching said surface.

2. The proximity operation X-ray imaging apparatus, according to claim 1, further comprising:

a second X-ray irradiation element; and a rotation mechanism that rotates wherein said main unit and said flat panel detector are configured to rotate around a central-axis facing a horizontal direction defined along a direction of said table.

* * * * *